United States Patent [19]

Coronelli et al.

[11] Patent Number: 4,476,111

[45] Date of Patent: Oct. 9, 1984

[54] ANTIBIOTIC S/433 AND PROCESS FOR ITS PREPARATION

[75] Inventors: Carolina Coronelli; Angelo Borghi, both of Milan; Giorgio Pirali, Saronno; Giovanni Mistrello, Milan, all of Italy

[73] Assignee: Gruppo Lepetit S.p.A., Milan, Italy

[21] Appl. No.: 312,486

[22] Filed: Oct. 19, 1981

[30] Foreign Application Priority Data

Oct. 25, 1980 [GB] United Kingdom ................. 8034448

[51] Int. Cl.$^3$ ......................... A61K 35/00; C12P 1/06
[52] U.S. Cl. ...................................... 424/119; 435/169
[58] Field of Search ......................... 424/119; 435/169

[56] References Cited

U.S. PATENT DOCUMENTS 4,173,629 11/1979 Dreyfuss et al. .................... 424/119
4,296,101 10/1981 Weisenborn et al. ............... 424/119

Primary Examiner—Jerome D. Goldberg
Attorney, Agent, or Firm—William J. Stein; Stephen L. Nesbitt; Gary D. Street

[57] ABSTRACT

A new antibiotic, designated S/433, is disclosed which is produced in a microbiological fermentation under controlled conditions using a new strain of Streptomyces. This new antibiotic is active against gram-positive and gram-negative bacteria and is also active in inhibiting the growth of transplanted tumors.

4 Claims, 2 Drawing Figures

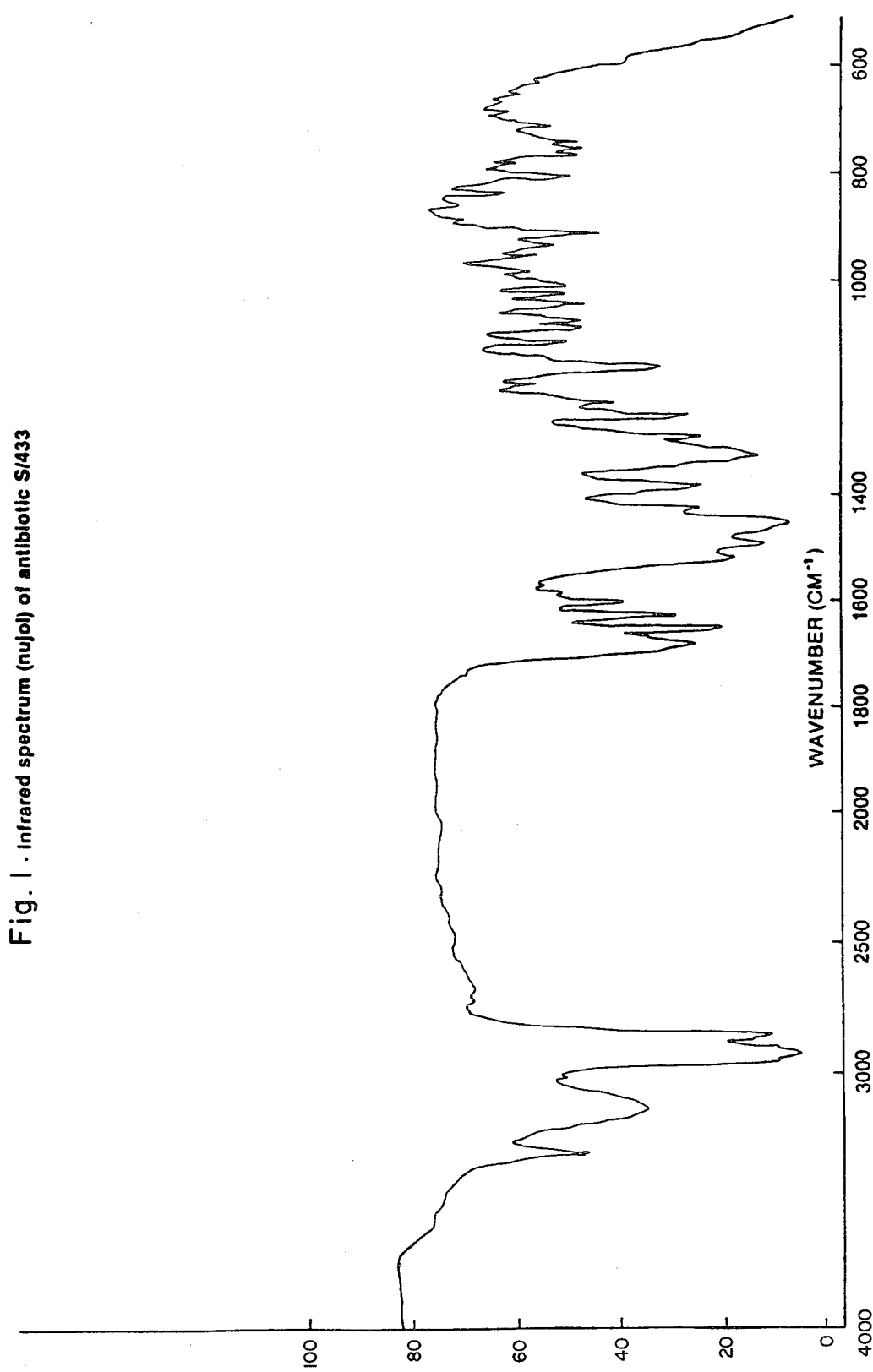
Fig. 1 - Infrared spectrum (nujol) of antibiotic S/433

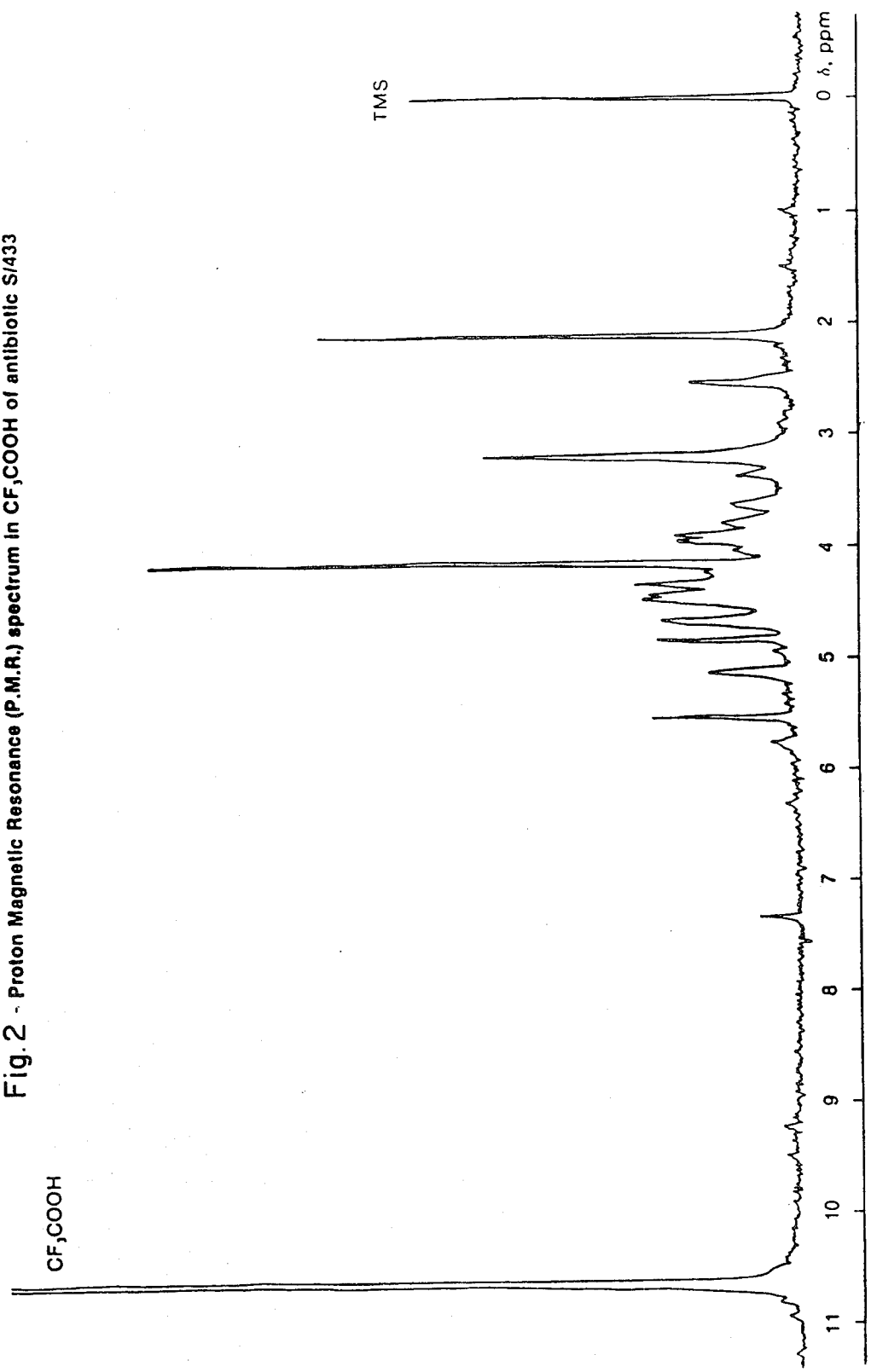

ANTIBIOTIC S/433 AND PROCESS FOR ITS PREPARATION

BRIEF SUMMARY OF THE INVENTION

The present invention relates to a new antibiotic substance arbitrarily designated herein as Antibiotic S/433 and, to a process for producing it by cultivation of a fermenting strain of the Streptomyces genus.

DETAILED DESCRIPTION OF THE INVENTION

Antibiotic S/433, in fact, besides inhibiting the growth of certain pathogenic organisms, especially gram-positive and gram-negative bacteria, shows outstanding anti-tumor properties against transplanted tumors.

As stated above, antibiotic S/433 is produced by cultivation of a fermenting strain of the Streptomyces genus. A culture of this strain, which was isolated from a soil sample collected in India, has been deposited on July 16, 1980, with the permanent culture collection of ATCC (American Type culture Collection—12301 Parklawn Drive, Rockville, Md.—20852 U.S.A.) where it has been accorded the accession number ATCC 31668.

The characteristics of this strain, Streptomyces sp. ATCC 31668, are given in the following paragraphs.

Morphology

The strain Streptomyces sp. ATCC 31668 grows well on various nutrient media. In oatmeal agar the colonies show regular contours (2–3 mm in diameter) and a central protuberance.

At microscopic examination the aerial mycelium appears to be formed of branched hyphae with spiral spore chains. The spores are non-mobile, spherical to ellipsoidal, 2.5×3 μm in size.

Cultural characteristics

Table 1 reports the cultural characteristics of Streptomyces sp. ATCC 31668 cultivated on various standard media suggested by Shirling and Gottlieb (Intern. J. System. Bact. 16, 313–340 (1966)) and other common media. The cultural characteristics were determined after 6 to 14 days of incubation at 30° C.

TABLE 1

The number of some of the culture media refers to those given by Shirling and Gottlieb in Methods for characterization of Streptomyces species - Intern. J. System. Bact. 16, 313-340 (1966).

| Culture medium | Cultural characteristics |
| --- | --- |
| Yeast-extract-malt agar (Medium no. 2) | Abundant growth with wrinkled surface light orange 10 B 2. Abundant aerial mycelium with spores. Pink soluble pigment |
| Oat Meal Agar (Medium no. 3) | Good growth with smooth whitish surface 10 A/1. Abundant spores production |
| Starch agar (Medium no. 4) | Moderate growth with whitish smooth surface |
| Glycerol-aspargine agar (Medium no. 5) | Abundant growth with rough whitish surface. Scarce spores production |
| Peptone-yeast extract-iron agar (Medium no. 6) | Abundant growth with smooth yellowish surface. Scarce spores production |
| Tyrosine agar | Abundant growth with wrinkled surface light orange 10 B/2. Abundant aerial mycelium with spores. Tyrosinase production positive |
| Nutrient agar | Abundant growth with smooth surface 12 C/3. Abundant spores production |
| Hickey and Tresner's agar: | Abundant growth with smooth surface gray to brown. Massive spore production |
| Bennett's agar | Abundant growth with wrinkled ivory surface 10 B/2. Abundant spores production. |
| Calcium malate agar | Moderate growth with smooth thin surface whitish to gray |
| Sabouraud | Abundant growth with smooth surface reddish 3 E/12. Abundant aerial mycelium with spores. Reddish soluble pigment |
| Skim-milk | Moderate growth with whitish smooth surface |
| Agar-H$_2$O | Very scant growth |
| Czapek glucose agar | Abundant growth with rough, whitish surface. Abundant aerial whitish mycelium with spores |
| Czapek sucrose agar | Scarce growth with thin whitish surface |
| Potato agar | Abundant growth with rough surface gray-to-brown. Abundant aerial mycelium with spores |
| Egg-albumin | Moderate growth with smooth whitish surface |
| Glucose asparagine agar | Good growth with smooth whitish surface |

Carbon utilization

Table II reports the utilization of carbon sources examined according to the method of Pridham and Gottlieb (J. Bact., 107, 1948)

TABLE II

| Carbon source | Utilization |
| --- | --- |
| Inositol | + |
| Fructose | + |
| Rhamnose | + |
| Mannitol | + |
| Xylose | + |
| Raffinose | − |
| Arabinose | + |
| Sucrose | + |
| Glucose | + |
| Mannose | + |
| Lactose | + |
| Salicin | + |
| Cellulose | − |

+ means positive utilization
− means no growth

Physiological characteristics

Table III reports the physiological characteristics of the strain Streptomyces sp. ATCC 31668.

TABLE III

| Test | Results |
| --- | --- |
| Hydrolysis of starch | negative |
| Calcium malate solubilization | positive |
| H$_2$S formation | negative |
| Liquefaction of gelatin | negative |
| Casein hydrolysis | negative |
| Tyrosinase production | positive |

TABLE III-continued

| Test | Results |
|---|---|
| Cellulose decomposition | negative |
| Litmus milk { peptonization | positive |
| coagulation | negative |

As in the case with other organisms, the characteristics of the S/433-producing culture, Streptomyces sp. ATCC 31668 are subject to variation. For example, artificial variants and mutants of the ATCC 31668 strain may be obtained by treatment with various known mutagens such as ultraviolet rays, X-rays, high frequency waves, radioactive rays and chemicals. All natural and artificial variants and mutants which belong to this Streptomyces species and produce antibiotic S/433 may be used in this invention.

For producing antibiotic S/433, the strain Streptomyces sp. ATCC 31668 is cultivated under aerobic conditions in an aqueous nutrient medium containing an assimilable source of carbon, an assimilable source of nitrogen and inorganic salts.

Said culture medium can be any of a number of nutrient media usually employed in the fermentation art, however certain media are preferred. Thus for instance preferred carbon sources are glucose, fructose, mannose, sucrose and the like in various grades of purity. Preferred nitrogen sources are peptone, soybean meal, meat extract, yeast extract, tryptone, amino acids and the like. Among the inorganic salts which can be used incorporated in the culture media, these are the customary soluble salts capable of yielding sodium, potassium, iron, zinc, cobalt, magnesium, calcium, ammonium, chloride, carbonate, sulfate, nitrate and the like ions.

For production of substantial quantities of antibiotic S/433 large jar fermentors are preferably employed. Because of the time lag in antibiotic production commonly associated with inoculation of large fermentors with the spore form of the organism, it is preferable to use a vegetative inoculum. The vegetative inoculum is prepared by inoculating a small volume of culture medium with the spore form or mycelial fragments of the organism to obtain a fresh, growing culture of the organism. The vegetative inoculum is then transferred to a larger fermentor. The medium used for the preculture can be the same as that employed for larger fermentations, but other media can be also employed.

The S/433-producing organism can be grown at temperatures between about 20° and 37° C. Optimum S/433 production appears to occur at temperatures of about 24°-30° C.

During the fermentation, antibiotic production can be followed by testing samples of the broth for antibiotic activity. Organisms known to be sensitive to antibiotic S/433 are useful for this purpose. One especially useful assay organism is *Staphylococcus aureus*. The bioassay is conveniently performed by the agar diffusion method on agar plates. Maximum production of antibiotic activity generally occurs between about the second and the third days. The antibiotic produced during fermentation of the S/433 producing organism are found mainly in the fermentation broth. A preferred method of recovering antibiotic S/433 is, therefore, by extraction of the filtered fermentation broth. Thus, after eliminating the mycelial cake by filtration, antibiotic S/433 is recovered from the filtered fermentation broth by extraction with an organic solvent in which the antibiotic substance is soluble and which is immiscible with the aqueous medium. The extraction is carried our after adjustment of the pH of the filtrate at about 7.5. Suitable organic solvents for the extraction are advantageously selected from lower halogenated hydrocarbons, alkanols containing from 4 to 6 carbon atoms or $(C_{1-4})$alkyl esters of lower aliphatic acids.

Antibiotic S/433 is then recovered from the extracting solvent by concentrating the organic extract to a small volume and cooling it to a temperature of about 0°-10° C. Antibiotic S/433 which thus precipitates is recovered by filtration and purified by crystallization from a suitable solvent.

Antibiotic S/433 is an orange-red crystalline substance which decomposes on heating with no well defined melting point. Its colour turns to dark orange-red at 150° C. and to black at 200° C.

It is soluble in dimethylformamide, dimethylsulfoxide, acetic acid; is slightly soluble in chloroform, methylene chloride; insoluble in water, methanol, petroleum ether, ethyl ether.

Elemental analysis of antibiotic S/433 indicates the following approximate percentage composition (as an average of several analyses): carbon, 57.88%; hydrogen, 5.33%; nitrogen; 9.51%; oxygen (by difference), 27.28%.

The infrared absorption spectrum of antibiotic S/433 in nujol is shown in FIG. 1 of the accompanying drawings. The following absorption maxima are observed (in $cm^{-1}$): 3310, 3140, 3020, 2950 (nujol), 2920 and 2860 (nujol), 1680, 1655, 1630, 1605, 1520, 1495, 1460 (nujol), 1425, 1380 (nujol); 1330, 1325, 1290, 1250, 1225, 1190, 1160, 1140, 1110, 1085, 1070, 1040, 1020, 1005, 980, 970, 950, 910, 880, 850, 830, 800, 780, 765, 750, 740, and 710.

The ultraviolet absorption spectrum of antibiotic S/433 exhibits the following absorption maxima:

(a) in 0.1N hydrochloric acid: 268 nm ($E_1 \, _{cm}1\% = 414$); 315 nm ($E_1 \, _{cm}1\% = 335$); 322 nm (shoulder)

(b) in phosphate buffer pH 7.38: 266 nm ($E_1 \, _{cm}1\% = 414$); 321 nm ($E_1 \, _{cm}1\% = 326$);

(c) in phosphate buffer pH 9.3: 266 nm ($E_1 \, _{cm}1\% = 403$); 322 nm ($E_1 \, _{cm}1\% = 326$)

The polarographic curve of antibiotic S/433 suspended in a mixture dimethylformamide/acetate buffer pH 5.4 shows two waves with half-wave potentials of $-0.16$ and $-0.51$ V. Antibiotic S/433 dissolved in methylcellosolve:water 10:15, when titrated with 0.01N NaOH shows one ionizable function with $pK_a = 7.8$.

The compound dissolved in glacial acetic acid, when titrated with 0.01N HClO$_4$ shows two titration slopes corresponding to two ionizable basic functions.

Antibiotic S/433 shows the following characteristics reactions:

| | |
|---|---|
| Tollens | negative |
| Fehling | negative |
| Anthrone | negative |
| H$_2$SO$_4$ conc. | negative |
| KMnO$_4$ aqueous | positive |
| Ninhydrin (after acidic hydrolysis) | positive |

The R$_f$ values of antibiotic S/433 in paper chromatography using different elution systems, are given in the following Table.

TABLE IV

Chromatographic behaviour (Whatman no. 1 paper) of antibiotic S/433

| Elution system | $R_f$ values |
| --- | --- |
| n-butanol saturated with phosphate buffer pH 6.0 | 0.0–0.2 |
| n-butanol saturated with water + 2% p-toluenesulfonic acid | 0.0–0.2 |
| n-butanol saturated with water + 2% NH$_4$OH | 0.0 |
| phosphate buffer pH 6 saturated with n-butanol | 0.7 |
| n-butanol-methanol-water (40:10:20) | 0.4 |
| n-butanol-acetic acid-water (2:1:1) | 0.75 |

The $R_f$ values of antibiotic S/433 in two thin-layer chromatographic systems are listed hereinbelow

| Elution system (v/v) | $R_f$ |
| --- | --- |
| 2% NaH$_2$PO$_4$:CH$_3$CN 6:4 pH 6.5 | 0.45 (on silicagel 60F$_{254}$ silanized plates) |
| chloroform:methanol:acetic acid (80:20:5) | 0.38 (on silicagel 60F$_{254}$ plates) |

The Proton Magnetic Resonance (PMR) spectrum of antibiotic S/433 in CF$_3$COOH which is given in FIG. 2 of the accompanying drawings exhibits the following peaks ($\delta$ units): 2.12 (s); 2.5–2.6 (m); 3.0–3.4 (m); 3.5–4.7 (m); 4.12 (s); 4.82 (s); 5.1–5.2 (m); 5.51 (s). (s=singlet; m=multiplet).

Antibiotic S/433 is an antibiotic agent active against gram-positive and gram-negative bacterial strains; its activity is particularly high against gram-positive bacteria and *M. gallisepticum*.

The in vitro antibacterial activity of antibiotic S/433 is summarized in Table V below (antibiotic S/433 was dissolved in dimethylformamide to a concentration of 10,000 μg/ml and further diluted with M/15 phosphate buffer pH 7.38. Minimal inhibitory concentrations (M.I.C.s) were determined using two-fold serial dilutions in broth):

TABLE V

| Organism | M.I.C. (μg/ml of antibiotic S.433) |
| --- | --- |
| *Staphylococcus aureus* ATCC 6538 | 0.012 |
| *Streptococcus pyogenes* C 203 | 0.001 |
| *Diplococcus pneumoniae* UC 41 | 0.001 |
| *Clostridium perfringens* ISS 30543 | 0.8 |
| *Proteus vulgaris* X19H ATCC 881 | 0.2 |
| *Escherichia coli* SKF 12140 | 0.1 |
| *Pseudomonas aeuriginosa* ATCC 10145 | 0.4 |
| *Candida albicans* SKF 2270 | 50 |
| *Tricophyton mentagrophytes* SKF 17140 | 100 |
| *Mycobacterium tuberculosis* H$_{37}$R$_v$ ATCC 9360 | 1.6 |
| *Mycoplasma gallisepticum* H 21 C.Z.B. | 0.05 |
| *Trichomonas vaginalis* | 0.8 (while the minimal Trichomonicidal concentration was 6.2 μg/ml) |

As stated before, antibiotic S/433 shows very interesting anti-tumor properties against transplanted tumors. The antitumor activity of antibiotic S/433 was tested both in vitro and in vivo according to the methodology described below:

In vitro experiments: P$_{388}$ murine leukemia cells were maintained in suspension in RPMI 1640 medium (see Moore et al.—Journal Am. Med. Assoc. 199, 8, pages 87 to 92 (1967)), supplemented with 10% fetal calf serum, antibiotics (penicillin 100 IU/ml, streptomycin 100 μg/ml), 2 mM L-glutamine, and $2\times10^{-5}$M 2-mercaptoethanol, at 37° C. in humidified atmosphere with 5% CO$_2$. To evaluate the in vitro activity of antibiotic S/433, the compound was dissolved in dimethylformamide and then diluted in sterile saline to a final concentration of dimethylformamide of 0.05%. The IC$_{50}$ value of antibiotic S/433 i.e. the concentration required for inhibiting of 50% the cellular growth with respect to controls, was about 50 ng/ml. Viable cell count by the tripan blue exclusion method, performed as described by Geran et al., in Cancer Chem. Rep. Part 3, 3, 17, (1972), was used as a measure of growth inhibition.

6-Mercaptopurine, included as a positive control, showed an IC$_{50}$ of about 1.0 μg/ml.

In vivo experiments (the in vivo testing has been carried out at the National Cancer Institute of Bethesda, Md.—U.S.A.):

In a preliminary screening the anti-tumor activity of antibiotic S/433 in vivo was tested with transplanted P$_{388}$ tumor bearing mice. In this assay, $10^6$ tumor cells were implanted intraperitoneally in CDF$_1$ mice. Antibiotic S/433, suspended in methocel, was injected subcutaneously with intermittent treatment, on day 1, 5, and 9, starting 24 hours after tumor implantation.

According to the National Cancer Institute protocols (see Geran et al., Cancer Chem. Rep. Part 3, 3, 17, 1972) the results obtained in these experiments are expressed as a percentage of control survival time (T/C). According to the criteria followed at NCI for the evaluation of the results obtained in this test, a reproduced T/C $\geq$ 125% is considered worthy of further study. At the dosage of 5 mg/Kg, the T/C value for antibiotic S/433 was 136%. 5-Fluorouracil, at the dose of 60 mg/Kg was employed in this test as the positive control giving a T/C=168%.

In a different test, still aimed at evaluating the activity of antibiotic S/433 against transplanted fluid tumors, the new compound was tested against Lymphocytic Leukemia L 1210. In this test, antibiotic S/433, at the dose of 10 mg/kg, gave a T/C of 130%.

Furthermore antibiotic S/433 was tested, still in mice, against some transplanted solid tumors, giving highly positive results against Colon 38 tumor and CD 8F1 Mammary tumor both in male and female mice.

More particularly, at the dose of 20 mg/kg, antibiotic S/433 caused a 83% reduction of the weight of the colon transplanted tumor in the treated animals over the controls; at the dose of 12.5 mg/Kg, gave a 91% reduction of the weight of the transplanted mammary tumor in female mice and at the dose of 25 mg/Kg, a 72% reduction of the weight of the mammary tumor in male mice. Highly positive results have been obtained also in the LX-1 Lung Xenograft test wherein at the dose of 5 mg/Kg antibiotic S/433 produced a 87% reduction of the weight of the tumor. All these tests and the evaluation of the results obtained have been performed according to the established NCI Protocols.

In order to illustrate more fully the process of the present invention, the following examples are provided.

EXAMPLE 1

Fermentation of the strain Streptomyces sp. ATCC 31668

A culture of Streptomyces sp. ATCC 31668 is precultured by growing the strain in a shake-flask culture having the following composition

| | |
|---|---|
| meat extract | 0.3 g |
| yeast extract | 0.5 g |
| tryptone | 0.5 g |
| soluble starch | 2.4 g |
| glucose | 0.1 g |
| $CaCO_3$ | 0.4 g |
| Tap water | 100 ml |

The flasks are shaken for about 48 hours at 25° C. and then the precultures are used to inoculate jar fermentors each containing 1 liter of the following nutrient medium

| | |
|---|---|
| peptone | 4 g |
| meat extract | 4 g |
| sodium chloride | 2.5 g |
| yeast extract | 1 g |
| Soybean meal | 10 g |
| Dextrose | 25 g |
| $CaCO_3$ | 5 g |
| Tap water | 1000 ml |

The fermentation batches are incubated aerobically with stirring at 25° C. At intervals, the antibiotic activity is assayed microbiologically by the agar diffusion method using *Staphylococcus aureus* as the test organism. The maximum activity is reached after 40 to 60 hours of fermentation.

EXAMPLE 2

Recovery of antibiotic S/433

The fermentation broth prepared as described in Example 1 is filtered and the mycelial cake is discarded. The filtrate is adjusted to pH 7.5 by the addition of 1N HCl and extracted twice with a half volume of dichloromethane. The organic extracts are combined and concentrated to about 1/50 of the original volume. The organic concentrate is allowed to stand overnight at 4° C. and the precipitate which forms, as orange-red needles, is recovered by filtration and dried under vacuum at room temperature. Antibiotic S/433 thus obtained is purified by crystallization from chloroform.

We claim:

1. Antibiotic S/433 which is an orange-red crystalline material which is soluble in dimethylformamide, dimethylsulfoxide, or acetic acid; is slightly soluble in chloroform or methylene chloride; but is insoluble in water, methanol, petroleum ether, or ethyl ether; which, on heating to 150° C. changes its colour to dark orange-red and decomposes with no well defined melting point at 200° C.; and which has:

(A) an approximate elemental composition of 57.88 percent carbon, 5.33 percent hydrogen; 9.51 percent nitrogen, and (by difference) 27.28 percent oxygen;

(B) an infrared absorption spectrum in nujol with the following observable absorption maxima: 3310, 3140, 3020, 2950 (nujol), 2920 and 2860 (nujol), 1680, 1655, 1630, 1605, 1520, 1495, 1460 (nujol), 1425, 1380 (nujol), 1330, 1325, 1290, 1250, 1225, 1190, 1160, 1140, 1110, 1085, 1070, 1040, 1020, 1005, 980, 970, 950, 930, 910, 880, 850, 830, 800, 780, 765, 750, 740, and 710 $cm^{-1}$;

(C) an ultraviolet absorption spectrum with the following absorption maxima:

(a) in 0.1N hydrochloric acid: 268 nm ($E_1$ $_{cm}^{1\%}$=414); 315 nm ($E_1$ $_{cm}^{1\%}$=335); 322 (shoulder);

(b) in phosphate buffer pH 7.38: 266 nm ($E_1$ $_{cm}^{1\%}$=414); 321 nm ($E_1$ $_{cm}^{1\%}$=326);

(c) in phosphate buffer pH 9.3: 266 nm ($E_1$ $_{cm}^{1\%}$=403); 322 nm ($E_1$ $_{cm}^{1\%}$=326);

(D) a titratable group with a $pK_a$ value of 7.8 in methylcellosolve:water 10:15

(E) two polarographic waves with $E_{\frac{1}{2}}$=−0.16 and −0.51 v; (suspended in dimethylformamide/acetate buffer pH 5.4).

(F) the following $R_f$ values in the paper-chromatographic systems indicated below (with Whatman no. 1 paper)

| Solvent system | $R_f$ values |
|---|---|
| n-butanol saturated with phosphate buffer pH 6.0 | 0.0–0.2 |
| n-butanol saturated with water + 2% p-toluenesulfonic acid | 0.0–0.2 |
| n-butanol saturated with water + 2% $NH_4OH$ | 0.0 |
| phosphate buffer pH 6.0 saturated with n-butanol | 0.7 |
| n-butanol:methanol:water (40:10:20) | 0.4 |
| n-butanol:acetic acid:water (2:1:1) | 0.75 |

(G) the following $R_f$ values in the thin-layer chromatographic systems indicated below:

| Solvent system (v/v) | $R_f$ values |
|---|---|
| 2% $NaH_2PO_4$:$CH_3CN$ 6:4 (pH 6.5) | 0.45 (on silica gel 60$F_{254}$ silanized plates) |
| chloroform:methanol:acetic acid (80:20:5) | 0.38 (on silica-gel 60$F_{254}$ plates) |

(H) the following characteristic reactions:

| | |
|---|---|
| Tollens | negative |
| Fehling | negative |
| Anthrone | negative |
| $H_2SO_4$ conc. | negative |
| $KMnO_4$ aqueous | positive |
| Ninhydrin (after acidic hydrolysis) | positive |

(I) A proton Magnetic Resonance spectrum which exhibits the following peaks (in $CF_3COOH$, δ units): 2.12 (s); 2.5–2.6 (m); 3.0–3.4 (m); 3.5–4.7 (m); 4.12 (s); 4.82 (s); 5.1–5.2 (m); 5.51 (s).

2. A process for manufacturing antibiotic S/433 as defined in claim 1, which comprises cultivating a strain of Streptomyces sp. ATCC 31688 in a culture medium containing assimilable sources of carbon and nitrogen, and inorganic salts under submerged conditions until a substantial amount of antibiotic activity is produced.

3. The process of claim 2 which includes the additional step of separating antibiotic S/433 from the culture medium.

4. The process of claim 3 wherein the separation of antibiotic S/433 from the culture medium is carried out by extracting the filtered fermentation broth with an organic solvent, selected from the group consisting of lower halogenated hydrocarbons, ($C_{4-6}$)alkanols and ($C_{1-4}$)alkyl esters of lower aliphatic acids.

* * * * *

UNITED STATES PATENT AND TRADEMARK OFFICE
CERTIFICATE OF CORRECTION

PATENT NO. : 4,476,111

DATED : October 9, 1984

INVENTOR(S) : Carolina Coronelli; Angelo Borghi

It is certified that error appears in the above-identified patent and that said Letters Patent is hereby corrected as shown below:

At Column 6, Line 55, the Patent reads: "colon transplanted tumor" and should read --transplanted colon tumor--.

Signed and Sealed this

Twenty-third Day of April, 1991

Attest:

HARRY F. MANBECK, JR.

*Attesting Officer*    *Commissioner of Patents and Trademarks*